(12) United States Patent
Lassetter et al.

(10) Patent No.: US 8,660,856 B2
(45) Date of Patent: Feb. 25, 2014

(54) HEALTHCARE SERVICE MANAGEMENT USING A CENTRALIZED SERVICE MANAGEMENT MODULE

(75) Inventors: J. Kipp Lassetter, Park City, UT (US); Jared Crapo, Sandy, UT (US); Jordan Meyerowitz, Scottsdale, AZ (US); Lilian T. Myers, Apopka, FL (US); Ashish V. Shah, Chicago, IL (US)

(73) Assignee: Medicity, Inc., Salt Lake City, UT (US)

( * ) Notice: Subject to any disclaimer, the term of this patent is extended or adjusted under 35 U.S.C. 154(b) by 515 days.

(21) Appl. No.: 12/362,336

(22) Filed: Jan. 29, 2009

(65) Prior Publication Data

US 2009/0222283 A1 Sep. 3, 2009

Related U.S. Application Data

(60) Provisional application No. 61/025,195, filed on Jan. 31, 2008.

(51) Int. Cl.
*G06Q 10/00* (2012.01)
(52) U.S. Cl.
USPC .................................................. 705/2; 705/3
(58) Field of Classification Search
CPC ............................... G06Q 50/22; G06Q 50/24
USPC ............................................... 340/573; 705/2
See application file for complete search history.

(56) References Cited

U.S. PATENT DOCUMENTS

| | | | |
|---|---|---|---|
| 2003/0046304 A1* | 3/2003 | Peskin et al. ............... | 707/104.1 |
| 2003/0088440 A1* | 5/2003 | Dunn ............................... | 705/3 |
| 2004/0172307 A1* | 9/2004 | Gruber ............................. | 705/3 |
| 2006/0229918 A1* | 10/2006 | Fotsch et al. ..................... | 705/3 |
| 2007/0035403 A1* | 2/2007 | Krishna et al. ............. | 340/573.1 |
| 2007/0162307 A1* | 7/2007 | Austin et al. ..................... | 705/2 |
| 2007/0226010 A1* | 9/2007 | Larsen ............................. | 705/2 |
| 2008/0275741 A1* | 11/2008 | Loeffen ........................... | 705/5 |
| 2008/0300926 A1* | 12/2008 | Di Costanzo et al. .......... | 705/5 |
| 2009/0125358 A1* | 5/2009 | Reynard ........................... | 705/8 |
| 2009/0144086 A1* | 6/2009 | Toleti et al. ....................... | 705/3 |
| 2009/0164236 A1* | 6/2009 | Gounares et al. ................ | 705/2 |

FOREIGN PATENT DOCUMENTS

WO WO2005103992 * 3/2005
WO WO 2005/103992 A2 11/2005

OTHER PUBLICATIONS

PCT International Search Report and Written Opinion, PCT/US09/32579, Jun. 1, 2009, 8 pages.

* cited by examiner

*Primary Examiner* — Elaine Gort
*Assistant Examiner* — Jonathan K Ng
(74) *Attorney, Agent, or Firm* — Patent Law Works LLP

(57) ABSTRACT

A system and method for scheduling or managing receipt of healthcare services are disclosed. A centralized service management module is coupled to one or more client devices and to one or more service providers, such as healthcare providers or insurance providers. The centralized service management module receives an interaction, such as an appointment request, from a client device or a service provider associated with healthcare services. The centralized service management module associates a service provider with the interaction based on a stored user profile. The interaction is then transmitted by the centralized service management module to the associated service provider, which provides data associated with a healthcare product or service associated with the interaction to the centralized service management module. The data is stored in the user profile and transmitted, buy the centralized service management module, to a client device using a communication protocol specified by the user profile.

38 Claims, 5 Drawing Sheets

HEALTHCARE SERVICE MANAGEMENT USING A CENTRALIZED SERVICE MANAGEMENT MODULE

CROSS REFERENCE TO RELATED APPLICATIONS

This application claims the benefit, under 35 U.S.C. §119 (e) of U.S. Provisional Application No. 61/025,195, filed Jan. 31, 2008, which is incorporated by reference herein in its entirety.

BACKGROUND

1. Field of Art

The present invention generally relates to the field of healthcare services, and more specifically, to managing healthcare products or services.

2. Description of the Related Art

Despite advancements in healthcare services, many healthcare consumers do not visit healthcare providers for routine care. Frustration with wait times, appointment availability and lack of feedback from healthcare providers discourages many healthcare consumers from pursuing medical care until treatment is necessary. While healthcare consumers desire to maintain a high level of health and wellness, inconveniences associated with receiving healthcare services typically cause healthcare consumers to postpone preventative or routine healthcare services.

Conventionally, healthcare consumers contact a healthcare provider to schedule an appointment for visiting the healthcare provider's office for treatment and then supply the healthcare provider with demographic information, such as medical history or insurance information, while visiting the healthcare provider. Because healthcare providers seek to maximize the number of healthcare consumers seen and the variable time for many healthcare procedures, despite scheduling an appointment in advance, healthcare consumers frequently encounter long wait times when visiting a healthcare provider. These long wait times inconvenience many healthcare consumers, causing them to postpone healthcare treatments until necessary because of injury or illness.

Additionally, to provide high-quality healthcare services, or related services such as pharmaceutical services, service providers need efficient and reliable access to various types of healthcare records. However, healthcare records are generally maintained by various sources which often use a proprietary or unique format to maintain healthcare records. For example, any one of a hospital, a healthcare organization, a clinic, a lab, an insurance company or a pharmacy may need access to healthcare consumer information maintained by a different source. The different data storage formats can delay retrieval of data by different healthcare services because of overhead associated with reformatting retrieved data.

Additionally, individual healthcare providers, or other service providers, generally maintain healthcare consumer information and other healthcare records in a format designed for retrieval or access by the specific healthcare provider, or other service provider. This proprietary storage of healthcare consumer information and other healthcare records makes it difficult for healthcare consumers to seamlessly visit different healthcare providers or other service providers by complicating retrieval of healthcare consumer information or other healthcare records from different healthcare providers, or other service providers. Although healthcare consumers are increasingly mobile and often interact with various healthcare providers, or other service providers, retrieval of healthcare consumer information by different local, state, regional or national healthcare providers, or other service providers, is complicated by the presence of political issues among entities, the lack of cooperation between competing entities and the storage of medical information or other healthcare records in different formats by different healthcare providers and other service providers. Additionally, healthcare consumers currently have limited control over the type of information shared between different healthcare providers or other service providers.

Thus, conventional methods of obtaining healthcare services inconvenience healthcare consumers with long wait times and limited availability for services while making sharing of healthcare consumer records between various healthcare providers, or other service providers, involved in healthcare consumer treatment difficult.

SUMMARY

A system and method for scheduling or managing receipt of healthcare services are disclosed. A centralized service management module is coupled to one or more client devices and to two or more independent service providers, such as healthcare providers or insurance providers. The centralized service management module receives an interaction record associated with a healthcare product or service from a client device or a service provider. The interaction record describes one or more healthcare products or services provided by a service provider for a user. In one embodiment, the interaction record identifies a product or service, the service provider, a user associated with the product or service. For example, the centralized service management module receives an appointment request identifying a service, a user, a service provider, a date and time associated with the service and/or a location associated with the service provider, from a client device for a user to schedule receipt of healthcare services. The centralized service management module identifies a service provider and a user associated with the interaction record. The interaction record is then stored and associated with a stored user profile associated with the identified user, allowing the centralized service management module to maintain a centralized record of data exchanges or communications between a user and two or more independent service providers. The centralized service management module then transmits the interaction record to the associated service provider or to a client device associated with the user, which retrieves' data associated with the interaction, such as a date and time associated with an appointment for receiving a service or product, a suggested treatment, notification of a prescription refill or other data associated with healthcare products or services. The centralized service management module stores data received from the service provider and associates the data received from the service provider with the identified user profile. The centralized service management module then transmits the data from the service provider to one or more client devices according to one or more settings in the user profile. For example, a setting in the user profile identifies one or more communication protocols for transmitting data to a user, allowing user-customization of how data is received to increase the likelihood that a user receives the data. Thus, the centralized service management module allows user-customization of how data is communicated between a client device and a service provider so that the most convenient communication protocol is used.

In one embodiment, an interaction comprises an appointment request, allowing a user to schedule an appointment using the client device and the centralized service management module to exchange information with two or more independent service providers. For example, the centralized service management module receives an interaction record, such as an appointment request, from a client device, identifies a user profile and a service provider associated with the interaction record and transmits the appointment request to the associated service provider which performs an action associated with the interaction record, such as scheduling an appointment, and transmits data describing the action associated with the interaction record, such as data describing a scheduled appointment, to the centralized service management module. As another example, responsive to receiving a request from the client device to check-in for a scheduled appointment, the centralized service management module transmits data from the user profile associated with healthcare products or services to a service provider associated with the scheduled appointment.

In one embodiment, the user profile includes one or more settings identifying one or more subsets of data in the user profile associated with healthcare products or services. These settings allow user-specific customization of data from the user profile transmitted to the service provider. For example, a first setting identifies a first subset of data for transmission to the service provider while a second setting identifies a second subset of data that is not transmitted to the service provider. Hence, these settings allow user regulation of transmission of data associated with the user healthcare services or products to personalize the dissemination of user information among service providers. To simplify receipt of healthcare products or services, the centralized service management module communicates user data to a service provider without requiring user initiation of the data exchange, but allows the user to regulate the privacy of his or her data through settings in the user profile.

In another embodiment, the centralized service management module also receives data from a second, independent, service provider describing services or products provided by the second service provider to the user. Hence, the centralized service management module communicates with two or more different service providers. The centralized service management module associates this data from the second service provider with the appropriate user profile, allowing the centralized service management module to include additional data describing healthcare services or products provided by the second service provider, which is different from the first service provider, to a user. In an embodiment, the second service provider also authenticates the data received by the centralized service management module, such as by cryptographically signing the data, to verify the accuracy of the data.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF DRAWINGS

The disclosed embodiments have other advantages and features which will be more readily apparent from the following detailed description and the appended claims, when taken in conjunction with the accompanying drawings, in which:

DETAILED DESCRIPTION

Figure 1:
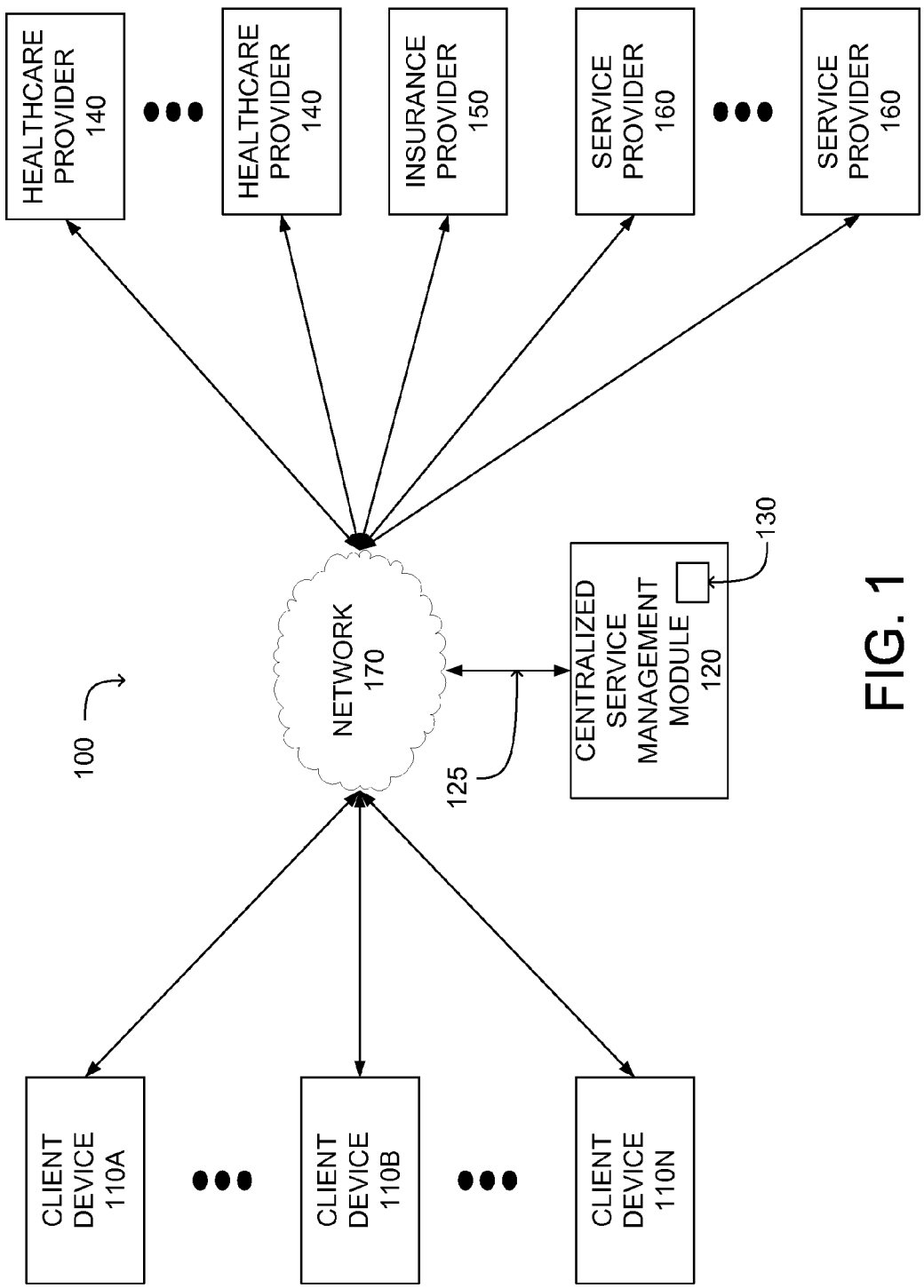
FIG. 1 is a block diagram of a system for centrally managing healthcare services according to an embodiment of the present invention.

A system and method for scheduling healthcare service appointments and accessing healthcare records using a centralized service management module are disclosed. For purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will be apparent from the description below. In addition, the present invention is not described with reference to any particular programming language. It will be appreciated that a variety of programming languages may be used to implement the teachings of the invention as described herein.

System Architecture

FIG. 1 is a block diagram of a system 100 for centrally managing healthcare services according to an embodiment of the present invention. The system 100 comprises one or more client devices 110A, 110B, 110N which communicate with a centralized service management module 120 using a network 170. In an embodiment, the centralized service management module 120 includes an individualized healthcare management module 130 which communicates with one or more service providers 160 using the network 170. The health care provider 140 and insurance provider 150, shown in FIG. 1 as communicatively coupled to network 170, are examples of service providers 160 which communicate with the individualized healthcare management module 130 However, these are merely examples and any entity providing products or services may be a service provider 160. In different embodiments, the system 100 may include different and/or additional components than those illustrated in FIG. 1.

The client devices 110A, 110B, 110N are one or more computing devices having data communication and/or data processing capabilities. Alternatively, the client devices 110A, 110B comprise one or more networks of computing devices, such as a local area network. Example client devices 110A, 110B, 110N include telephones, desktop computers, laptop computers, notebook computers, mobile or cellular telephone, portable digital assistants, smartphones or other similar devices. The system 100 enables use of different types of client devices 110, allowing a user to communicate with the network 170 using various client devices 110. For example, client device 110A comprises a desktop computer, client device 110B comprises a smartphone and client device 110N comprises a laptop computer, allowing access to network 170 from various devices using different types of communication channels. Different client devices 110A, 110B, 110N may use different protocols to communicate information, allowing network access using Internet Protocol (IP) packets, Short Message Service (SMS) messages, email, hypertext transfer protocol (HTTP) data, telephone calls, facsimile transmissions or other suitable communication protocols.

The centralized service management module 120 comprises one or more computing devices communicatively coupled to the network 170, via communication link 125, which receive data from one or more client devices 110 and/or two or more service providers 160 and transmit data to one or more client devices 110 and/or one or more service providers 160. For example, the centralized service management module 120 comprises a computing device, such as a hardware server, which receives data from one or more client devices 110 and two or more independent service providers 160. One or more users establish an account with the centralized service management module 120 and transmit data to the centralized service management module 120 using a client device 110. This information is stored by the centralized service management module 120 as one or more user profiles. Data from these user profiles is communicated from the centralized service management module 120 to one or more service providers 160 based on user preferences or commands, allowing the centralized service management module 120 to distribute information from one or more client devices 110 to one or more service providers 160 and vice versa.

Hence, the centralized service management module 120 simplifies information exchange between users of client devices 110 and one or more service providers 160. By using the centralized service management module 120, users may access relevant data from different client devices 110 in different locations while users of client devices 110 also regulate information about the user sent to a service provider 160 from the centralized service management module 120. By communicating with client devices 110 using the network 170, the centralized service management module 120 enables users to communicate with service providers 160 using a variety of communication protocols, as the centralized service management module 120 reformats data from client devices 110 into a protocol compatible with a service provider 160.

The centralized service management module 120 includes an individualized healthcare management module 130 for communicating information between one or more client devices 110 and a healthcare service provider 140, an insurance provider 150 or other service provider 160 supplying healthcare products or services via the network 170. The individualized healthcare management module 130 communicates data from the centralized service management module 120 to one or more service providers 160, allowing the service providers 160 to access information about one or more users when providing healthcare products or services. Commands or data received by the centralized service management module 120 from a client device 110 allow users to modify the data communicated between an individualized healthcare management module 130 and a service provider 160 using a client device 110. For example, the individualized healthcare management module 130 communicates healthcare-related data, such as appointment requests, medical history, demographic information or insurance information, from a user profile stored by the centralized service management module 120 to a healthcare provider 140 to facilitate user treatment by the healthcare provider 140. Additionally, the individualized healthcare management module 130 communicates data, such as suggested medical treatments based on demographic information and accepted medical guidelines, reminders of scheduled appointments or other data associated with healthcare products or services from a service provider 160 or healthcare service provider 140 to one or more client devices 110 to allow the service provider 160 or healthcare provider 160 to simplify providing services or products to a user. Although shown in FIG. 1 as included in the centralized service management module 120, in other embodiments the individualized healthcare management module 130 comprises a discrete module.

In one embodiment, the individualized healthcare management module 130 also receives healthcare data from a plurality of independent healthcare providers 140 or other service providers 160 and includes the received healthcare data in a user profile stored by the centralized service management module 120. Additionally, the individualized healthcare management module 130 communicates information received from healthcare provider 140 or service provider 160 to a client device 110. For example, the individualized healthcare management module 130 receives a notification message indicating that the healthcare provider 140 is ready for a user to arrive in person. This notification message is transmitted from the individualized healthcare management module 130 a client device 110 associated with the user via network 170. As another example, a service provider 160 generates a notification that a user's prescription has been refilled and transmits the notification to the individualized healthcare management module 130, which then transmits the notification to one or more client devices 110 via network 170. Hence, the individualized healthcare management module 130 simplifies communication between a user and a healthcare provider 140, allowing users to more easily manage and schedule receipt of healthcare services or products.

Two or more independent healthcare providers 140 are communicatively coupled to the network 170 and exchange information with the individualized healthcare management module 130 and/or centralized service management module 120 via the network 170. Healthcare providers 140 provide products or services relating to maintaining the physical or mental well-being of a user. Examples of a healthcare provider 140 include a hospital, a pharmacy, a physician office, a clinic, a medical laboratory, a diagnostic imaging facility, an outpatient surgery facility, a long-term care facility, an urgent care facility or other similar entity providing medical treatments. Additional examples of healthcare providers 140 include entities providing services ancillary to medical treatments, such as a physician or hospital rating service, a personal health record store, a health coach, a health bank, a health information provider, a health savings account, a flexible savings account, a health reimbursement arrangement, a medical savings account or similar entity providing services or goods associated with medical treatment. Communicatively coupling a plurality of independent healthcare providers 140 to the centralized service management module 120 via network 170 allows the centralized service management module 120 to receive data associated with healthcare services and/or products provided by disparate healthcare providers 140, enabling the centralized service management module 120 to provide a single location for a user to access data from unrelated healthcare providers 120 which simplifies user management of healthcare services and/or products.

In one embodiment, one or more insurance providers 150 are communicatively coupled to the network 170 in addition to the plurality of healthcare providers 140. The one or more insurance providers 150 communicate data with the plurality of independent healthcare providers 140, one or more client devices 110 and/or two or more service providers 160 using the individualized healthcare management module 130. Hence, the individualized healthcare management module 130 communicates claim information from a plurality of independent healthcare providers 140 or a plurality of independent service providers 160 to one or more insurance providers 150 for payment. Additionally, the individualized healthcare management module 130 receives data associated with a claim from the insurance provider 150 and communicates the data to a user through the network 170 and a client device 110.

In an embodiment, a plurality of independent service providers 160 are also communicatively coupled to the network 170 and exchange information with the centralized service management module 120. While a service provider 160 may provide medical products or services or provide goods or services related to medical treatment, a service provider 160 may also provide additional types of services. For example, a service provider 160 may comprise a financial institution, a travel agent, a scheduler or any other service which provides personalized services or products. Exchanging information with a plurality of independent service providers 160 allows the centralized service management module 120 to receive data from disparate and/or unrelated service providers 160 to provide a central location for storage and/or distribution of data from independent service providers 160. Hence, the centralized service management module 120 simplifies user communication with independent service providers 160 by centrally storing and maintaining user-specific data and interaction records describing user communication or contact with various service providers 160.

The network 170 transmits data or instructions between or among the client devices 110A, 110B, 100N the centralized service management module 120, the healthcare provider 140, the insurance provider 150, the service provider 160 and/or other devices (not shown). The network may comprise a conventional wireless data communication system, for example, general packet radio service (GPRS), IEEE 802.11 (or WiFi), IEEE 802.16 (or WiMax), Bluetooth, or any other suitable wireless communication system. Alternatively, the network may comprise a conventional wired data communication system, such as Ethernet, digital subscriber line (DSL), integrated services digital network (ISDN), or any other suitable wired communication system. In an embodiment, the network comprises a combination of a wireless communication system and a wired communication system. Hence, the network 170 transmits data using multiple protocols, such as email, HTTP, SMS, IP, 3G or any other data transmission protocol. Alternatively, the network is replaced by a peer-to-peer configuration where one or more devices or modules directly communicate with each other.

Figure 2:
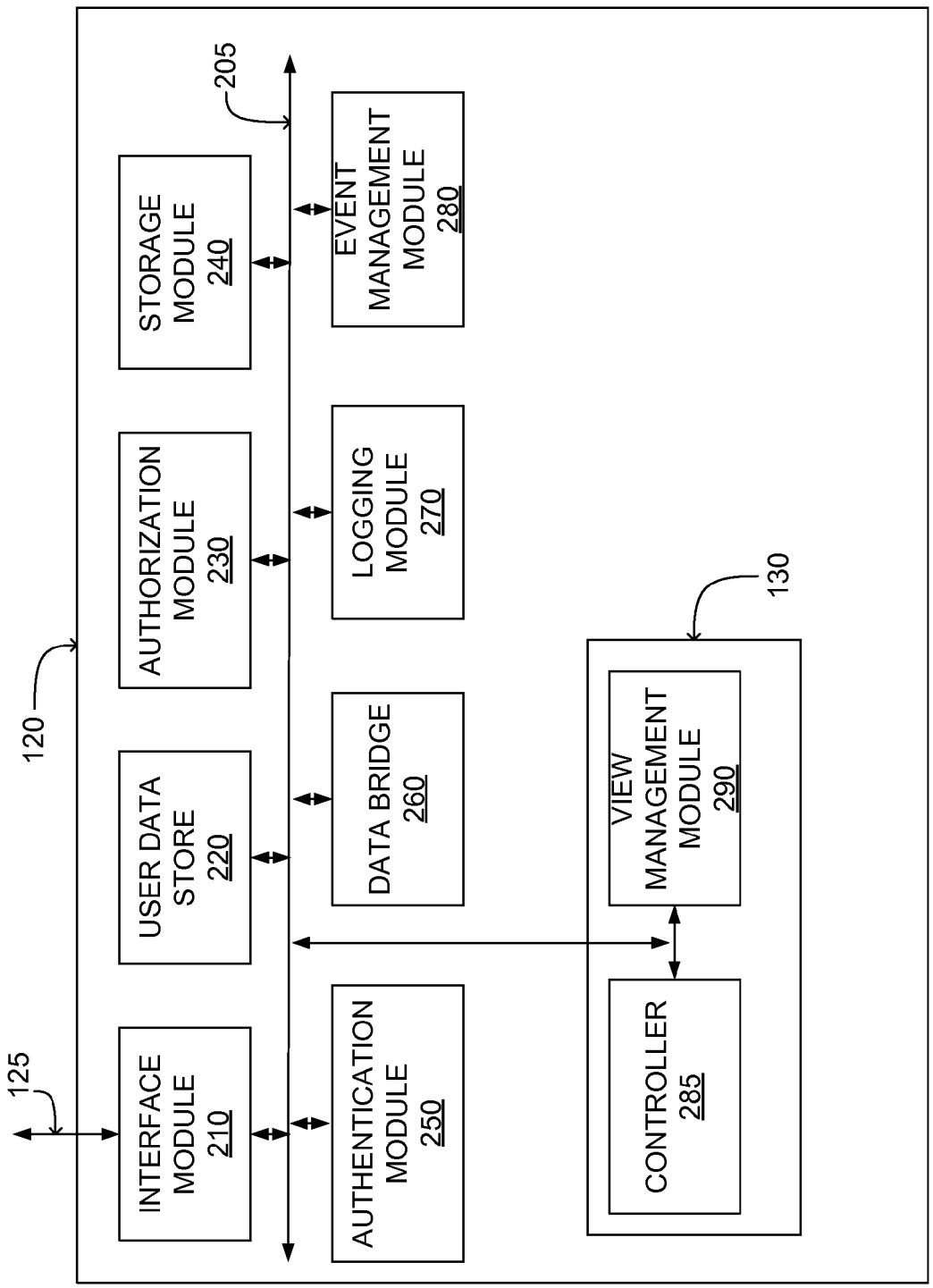
FIG. 2 is a block diagram of a centralized service management module including an individualized healthcare management module according to an embodiment of the present invention.

FIG. 2 is a block diagram of a centralized service management module 120 including an individualized healthcare management module 130 according to an embodiment of the present invention. In one embodiment, the centralized service management module 120 includes an interface module 210, a user data store 220, an authorization module 230, a storage module 240, an authentication module 250, a data bridge 260, a logging module 270 and an event management module 280 coupled by a bus 205. In the example embodiment shown in FIG. 2, the centralized service management module 120 includes an individualized healthcare management module 130 having a controller 285 and a view management module 290 coupled to the bus 205. Those of skill in the art will recognize that different embodiments can provide the functionality of FIG. 2 in different ways. For example, the components described below in conjunction with FIG. 2 are implemented as one or more software processes executable by a processor (not shown) and/or one or more firmware applications. The processes and/or firmware are configured to operate on one or more general purpose microprocessors or controllers, a field programmable gate array (FPGA), an application specific integrated circuit (ASIC) or a combination thereof. Alternatively, the components described below in conjunction with FIG. 2 are implemented using one or more processors having any one of various computing architectures including a complex instruction set computer (CISC) architecture, a reduced instruction set computer (RISC) architecture or an architecture implementing a combination of instruction sets. In another embodiment, the components described in conjunction with FIG. 2 comprise one or more software or firmware processes running on a general purpose computer hardware device. For example, as one or more software processes executed by a general purpose processor on a computing device. Moreover, other embodiments can include different and/or additional features and/or components than the ones described here.

The interface module 210 communicates data between the centralized service management module 120 and one or more client devices 110 or other devices via communication link 125. In an embodiment, the communication module 210 comprises a transceiver such as for infrared communication, Bluetooth communication, Global System for Mobile communications (GSM), General Packet Radio Service (GPRS)

communication, Enhanced Data Rates for GSM Evolution (EDGE) communication, Code Division Multiple Access (CDMA) communication, 3G communication, radio frequency communication or any other wireless communication technique. In an alternative embodiment, the interface module 210 comprises a conventional wired connection, such as Ethernet, Universal Serial Bus (USB) or other wired communication techniques. Alternatively, the interface module 210 comprises both a wired connection and a transceiver. The interface module 210 transmits and receives data, commands and/or information using one or more network protocols, such as Transmission Control Protocol (TCP), Internet Protocol (IP), Hypertext Transmission Protocol (HTTP), or other protocols capable of communicating data or information. Thus, the interface module 210 receives data from client devices in various formats, allowing users to exchange data or commands with the centralized service management module 120 in various formats using different types of client devices 110.

The user data store 220 is a persistent storage device, such as a hard disk drive or flash memory device which stores one or more user profiles. In an embodiment, the user data store also includes a non-persistent storage device, such as dynamic random access memory (DRAM), static random access memory (SRAM) or other device storing data for at least a limited time to allow rapid access to a subset of information for a limited amount of time. User profiles are stored in the user data store 220 and the user profiles include user credentials, preferences, settings or other user-specific information and each user profile is associated with a unique identifier corresponding to a user. For example, a user profile uses a login and password or other user credentials, to identify the user associated with the user profile.

The stored user profiles are associated with user credentials, such as a username and password, a personal identification code or similar data, that uniquely identify a user associated with a user profile and securing the user profile by verifying that credentials received from a client device 110 correspond to user credentials associated with a user profile. Hence, a first user is prevented from accessing or manipulating data stored in a user profile associated with a second user. For example, a received username and password pair or access code are compared to a username and password pair or access code included in the user profile to grant or deny access to the user profile. Alternatively, a single user profile may include data for a group of users. For example, a user profile may include information for a family, allowing more than one family member to access or modify the user profile. User credentials received by the centralized service management module 120 are compared to user credentials in the user data store 220 to grant or deny access to a user profile.

In an embodiment, the user data store 220 includes information associated with medical care or treatment of a user, such as a medical history, insurance information, demographic information or similar data for use by a healthcare provider 140 or a service provider 160. Thus the user data store 220 is a central location for users to store and/or manage data applicable to healthcare services, simplifying communication of this data to one or more healthcare service providers 140 or other service providers 160. The user profiles in the user data store 220 also allow configuration of user-specific settings, such as settings describing the communication protocols used by the centralized service management module 120 to communicate with the user's client devices 110. For example, a user-specific setting causes transmission of reminder messages via SMS or text messaging to a client device 110A and transmission of billing information to via email to the client device 110A. This allows the user to receive data from the centralized service management module 120 using different communication protocols, increasing the likelihood that a user receives the data from the centralized service management module 120. A user profile also includes one or more privacy settings, allowing user regulation of data transmitted from the centralized service management module 120 to a service provider 160.

The authorization module 230 comprises a storage device or a partition of a storage device, including data or instructions for managing user access to one or more service providers 160 or applications associated with one or more service providers 160. In one embodiment, the authorization module 230 associates a user profile with a service provider 160 or a healthcare provider 140 to allow communication of data from the user profile to the healthcare provider 140 or to the service provider 160. For example, the authorization module 230 stores login information, authorization information or other user credentials associated with a healthcare provider 140 or a service provider 160, allowing exchange of data from the user profile with the healthcare provider 140 or the service provider 160. The authorization module 230 allows users to modify the healthcare providers 140 or the service providers 160 authorized to access information or data from a user profile.

In an embodiment, the authorization module 230 also identifies a subset of data within a user profile accessible by a healthcare provider 140 or a service provider 160. This allows a user to regulate access to individual data within a user profile by the healthcare provider 140 or the service provider 160. For example, the authorization module 230 may allow a healthcare provider 140 to access a user's medical history and demographic information while preventing the healthcare provider 140 from accessing financial information associated with the user. Thus, the authorization module 230 regulates access to data within a user profile based on user preferences or settings.

The storage module 240 is a persistent storage device, such as a hard disk drive or flash memory device storing data or information. In an embodiment, the storage module 240 also includes a non-persistent storage device, such as dynamic random access memory (DRAM), static random access memory (SRAM) or other device storing data for at least a limited time, allowing rapid access to a data for a limited amount of time or storing data for temporary use. The storage module 240 includes data describing operation of the centralized service management module 120, such as operating system information, configuration data for the interface module 210 or other data describing configuration operation of one or more modules or components included in the centralized service management module 120. In an embodiment, the storage module 240 also stores data describing configuration or operation of the controller 285, further described below, to facilitate communication between the centralized service management module 120 and the plurality of healthcare providers 140 and/or the plurality of service providers 160. For example, the storage module 240 includes data describing how the controller 285 exchanges data with the plurality of healthcare providers 140 or the plurality of service providers 160. In various embodiments, the storage module 240 stores data using different techniques, such as relational storage, bucket storage, object storage or other storage methods.

The authentication module 250 includes data for authentication or verification of data included in the user profile. For example, the authentication module 250 includes instructions or data for cryptographically hashing, signing and/or encrypting data within a user profile. This allows a user to verify the authenticity of data included in a user profile or to encrypt data included in a user profile. In an embodiment, the authentication module 250 also includes data enabling a service provider 160 to authenticate data associated with a user provided by the service provider 160. This allows a service provider 160 to verify that data about a user originates from a particular source, such as a service provider 160. Hence, the authentication module 250 allows a user or service provider 160 to encrypt, sign or otherwise verify the origin of data received by the centralized service management module 120. In an embodiment, the authentication module 250 describes establishment of a secure communication channel between the centralized service management module 120 and the plurality of independent healthcare providers 140, the one or more insurance providers 150 and/or the two or more independent service providers 160, allowing secure communication of data between the centralized service management module 120 and the plurality of independent healthcare providers 140, the one or more insurance providers 150 and/or the two or more independent service providers 160.

The data bridge 260 includes one or more adapters for communicating with one or more service providers 160, one or more insurance providers 150 and/or one or more healthcare providers 140. The adapters enable the centralized service management module 120 to transmit data to a service provider 160, healthcare provider 140 or an insurance provider 150 in a format associated with the provider receiving the data. Additionally, the data bridge 260 adapters modify the format of data received from a service provider 160, an insurance provider 150 or a healthcare provider 140 to a standardized format used by the centralized service management module 120. Thus, the adapters included in the data bridge 260 allow the centralized service management module 120 to convert the format of received data or transmitted data, allowing the centralized service management module 120 to easily exchange data with a variety of providers, even when the providers use different methods to store data.

In an embodiment, the data bridge 260 also includes a storage device, such as a dynamic random access memory (DRAM), static random access memory (SRAM) or other non-volatile storage device that stores data for a limited time. The storage device stores data received from a healthcare provider 140, an insurance provider 150 or other service provider 160 in the centralized service management module 120. Using the data bridge to temporarily store storing data from a healthcare provider 140, an insurance provider 150 or other service provider 160 allows the centralized service management module 120 to more rapidly access the data during operation by locally storing data being used. In one embodiment, the data is removed from the storage device after a predefined time interval. Alternatively, the data is removed from the storage device when a connection with the healthcare provider 140, insurance provider 150 or other service provider 160 providing the data is closed. In an embodiment, the storage device is encrypted to secure the locally stored data.

The logging module 270 comprises a persistent storage device, such as a hard disk drive, a flash drive or similar device, which stores a log of events and actions performed by applications and/or users accessing the centralized service management module 120. Hence, the logging module 270 maintains a record of users, applications and/or service providers 160 accessing the centralized service management module 120, actions performed by the centralized service management module 120 and/or service providers 160 accessed by the centralized service management module 120. This allows subsequent verification of actions using the centralized service management module 120 and provides users with a method for verifying accesses and modifications to their associated user profiles. In one embodiment, data recorded by the logging module 270 is cryptographically signed or otherwise secured, making tampering with or alteration of logged data easier to subsequently identify. This allows the logging module 270 to maintain an accurate log of events and/or actions performed by the centralized service management module 120. In an embodiment, the logging module 270 also partitions logged data into discrete components to simplify subsequent reporting or analysis. For example, in addition to storing data describing an event or action, the logging module 270 identifies a user identifies associated with the event or action, temporal data indicating when the event or action occurred and a description, such as a text description or an identifier of the event.

The event management module 280 manages communication between the centralized service management module 120, client devices 110, the plurality of independent healthcare providers 140, the one or more insurance providers 150 and/or the plurality of independent service providers 160, configuration of the centralized service management module 120, interaction records describing communication between a client device and a plurality of service providers 160 or a plurality of healthcare providers 140 or other data communication events generated by the centralized service management module 120 or event configuring the centralized service management module 120. The event management module 280 allocates resources, such as storage capacity, processor time, interface module 210 settings or other configuration data to allocate centralized service management module 120 resources for communicating with different client devices 110, healthcare providers 140, insurance providers 150 or other service providers 160. In an embodiment, the event management module 280 allocates resources so the centralized service management module 120 completes actions associated with multiple users with minimal latency. Additionally, in another embodiment, the event management module 280 associates a priority with one or more events so the events are performed or completed in an order specified by the associated priority.

In one embodiment, the event management module 280 includes one or more fallback triggers associated with an event, so that a fallback trigger is executed if an event does not occur or if a condition associated with an event is not met. For example, if an appointment is scheduled and the centralized service management module 120 does not receive a check-in request associated with the scheduled appointment, the event management module 280 notifies the user that an appointment was missed and prompts the user to schedule a new appointment. Hence, the event management module 280 allows tracking of relationships between one or more events. In an embodiment, the event management module 280 also includes data specifying the timing of events, such as data specifying when a reminder is transmitted prior to an appointment. In one embodiment, the event management module 280 receives data from one or more service providers 160 and uses the received data to determine when to transmit reminders for services associated with different service providers 160, allowing service providers 160 to customize when reminders are transmitted.

In the example embodiment depicted by FIG. 2, the centralized service management module 120 also includes an individualized healthcare management module 130. The individualized healthcare management module 130 includes a controller 285 and a view management module 290 which communicate with the previously described components via bus 205. In other embodiments, however, the individualized healthcare management module 130 comprises a separate component that is communicatively coupled to the centralized service management module 120.

The controller 285 exchanges data between the individualized healthcare management module 130 and the healthcare provider 140, the insurance provider 150 or the service provider 160. By receiving data or commands from a client device 110 via the interface module 210, the controller 285 identifies a service provider 160, a healthcare provider 140 or an insurance provider 150 associated with the data or commands and then transmits the data or commands to the appropriate destination. The controller also receives data from a healthcare provider 140, an insurance provider 150 or other service provider 160 and associates the received data with a user profile for storage and/or transmission to a client device 110 associated with the user profile. In an embodiment, the controller 285 also includes authentication or login information, such as a certificate or a username and password pairing, for accessing the healthcare provider 140, the insurance provider 150 or other service provider 160, allowing access to the healthcare provider 140, the insurance provider 150 or other service provider 160 without manual entry of authentication or login information.

Additionally, the controller 285 obtains information from different service providers 160 for storage in the user data store 220 or storage module 240 to provide a central location for user access to data from a plurality of service providers 160. For example, the controller 285 retrieves insurance forms from an insurance provider 150 and retrieves medical forms, such as a patient intake form, from a service provider 160, allowing a user to complete the patient intake form and insurance forms prior to arrival at a healthcare provider 140 and review insurance claim submissions after receiving services or products from the healthcare service provider 140. By obtaining information from different service providers 160, the controller 285 provides a central location for a user to perform multiple tasks, unlike conventional methods which require a user to individually access each service provider 160.

The controller 285 can be implemented in many ways. For example, it is a software process executable by a processor (not shown) and/or a firmware application. The process and/or firmware is configured to operate on a general purpose microprocessor or controller, a field programmable gate array (FPGA), an application specific integrated circuit (ASIC) or a combination thereof. Alternatively, the controller 285 comprises a processor that has any one of various computing architectures including a complex instruction set computer (CISC) architecture, a reduced instruction set computer (RISC) architecture or an architecture implementing a combination of instruction sets. The controller 285 can comprise a single processor or multiple processors. Alternatively, the controller 285 comprises multiple software or firmware processes running on a general purpose computer hardware device.

The view management module 290 is communicatively coupled to the controller 285 and other components described above in conjunction with FIG. 2 via the bus 205. As the controller 285 receives data from one or more service providers 160, the view management module 290 modifies the format and/or appearance of the received data to a uniform format, simplifying user interaction or modification of the data. As different service providers 160 may differently store or format data, the view management module 290 reformats the received data, simplifying user interaction with the received data. Hence, the view management module 290 allows the individualized healthcare management module 130 to present and/or store disparate data using a standardized format or structure. For example, different healthcare providers 140 may differently store healthcare consumer records by placing information in different orders or storing information in different formats, the view management module 290 modifies the format of the received data so that information from different healthcare providers 140 or service providers is presented and/or stored in a standardized order and in a standardized format, simplifying later retrieval and review of the received information.

The authorization module 230, authentication module 250, data bridge 260, logging module 270, event management module 280, controller 285 and/or view management module 290, described above, can be implemented in many ways. For example, they can be one or more software processes executable by a processor (not shown) and/or a firmware application. The software and/or firmware can be configured to operate on a general purpose microprocessor or controller, a field programmable gate array (FPGA), an application specific integrated circuit (ASIC) or a combination thereof. Additionally, in embodiments, one or more of the authorization module 230, authentication module 250, data bridge 260, logging module 270, event management module 280, controller 285 and/or view management module 290 are combined so that a single module performs the functionality of a plurality of the above-described modules.

System Operation

Figure 3:
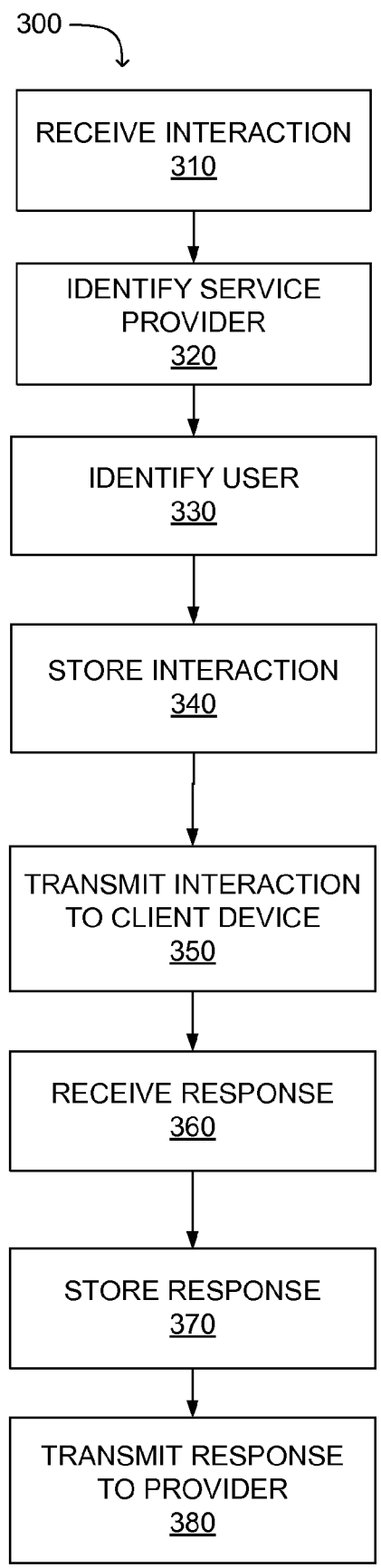
FIG. 3 is a flow chart of a method for healthcare service management by an individualized healthcare management module according to an embodiment of the present invention.

FIG. 3 is a flow chart of a method 300 for healthcare service management by an individualized healthcare management module 130 according to an embodiment of the present invention. In an embodiment, the steps of the method 300 are implemented by a controller 285 included in the centralized service management module 120 executing software or firmware instructions that cause the described actions. Those of skill in the art will recognize that one or more of the methods may be implemented in embodiments of hardware and/or software or combinations thereof. For example, instructions for performing the described actions are embodied or stored within a computer readable medium. Furthermore, those of skill in the art will recognize that other embodiments can perform the steps of FIG. 3 in different orders. Moreover, other embodiments can include different and/or additional steps than the ones described here.

The centralized service management module 120 receives 310 an interaction record from a service provider 160, a healthcare provider 150, an insurance provider 150 or a client device 110 via the interface module 210 or data bridge 280. An interaction record is associated with the interaction and includes data identifying a healthcare product or service such as a text description of the product or service or a code identifying the product or service, a user associated with the healthcare product or service, a provider identification number or other data identifying a service provider 160 or healthcare provider 140 associated with the healthcare product or service, a date and/or time associated with the interaction, a date and/or time associated with the healthcare product or service, a physical address associated with the service provider 160 or healthcare provider 140 or other data describing products or services provided by a service provider 160 or a healthcare provider 140. In an embodiment, the interaction report includes additional data, such as healthcare data associated with a user, such as diagnostic results, an appointment reminder, a request to schedule an appointment, healthcare recommendations, notification of completion of a pharmaceutical refill or other data associated with healthcare services and/or products. In one embodiment, the interaction record includes a text description of the services; however, in other embodiments, the interaction record includes a numeric code or other code identifying the services or other suitable description of the services. The interaction record also includes data identifying the user associated with the interaction, such as a healthcare consumer identifier, a login name, an email address, a phone number or other data uniquely identifying the user. In an embodiment, the interaction record includes additional data, such as a suggested desired date or time for the service, a range of dates or times for the service, hours of operation associated with the service provider 160, an indication of the priority of the interaction or other data associated with obtaining services from a service provider 160.

The controller 285 included in the individualized healthcare management module 130 within the centralized service management module 120 then identifies 320 a service provider 160 and identifies 330 a user associated with the received interaction record using data included in the interaction record. For example, the controller 285 compares the service identifier included in the interaction record with service identifiers stored in the storage module 240 of the centralized service management module 120 and compares a user identifier included in the interaction record with user identifies stored in the user data store 220. Alternatively, the controller 285 filters a listing of service providers 160 included in the storage module 240 using information in the interaction record, such as a recommended date or time or range of dates or times for the service, a maximum distance between the service provider 160 and the identified user associated with the interaction record or other data associated with obtaining or receiving services from a service provider 160 to identify 320 a service provider.

The centralized service management module 120 then associates the interaction record with the identified user profile and stores 340 the interaction in the user data store 220. In an embodiment, the centralized service management module 120 identifies the user associated with the healthcare product or service described by the interaction report and retrieves a user profile associated with the identified user. For example, the centralized service management module 120 compares a user identifier included in the interaction record with user identifiers included in the user data store 220 and retrieves a user profile from the user data store 220 corresponding to the user identifier included in the interaction record. This allows the stored user profile to provide a history of interactions between service providers 160 and a user by storing interaction records associated with the user. Hence, the individualized healthcare management module 130 provides a central location for a user to review communications to and from various independent service providers 160 or healthcare providers 140 using a user profile. After storage 340, the individualized healthcare management module 130, or centralized service management module 120, transmits 350 the interaction report, or a subset of data from the interaction report, to one or more client devices 110 associated with the identified user via the interface module 210. For example, the service provider 160 identifier or healthcare provider 140 identifier, a date and/or time associated with the healthcare product or service and a description of the healthcare product or service are retrieved from the interaction report and transmitted 350 to one or more client devices 110. Alternatively, an identifier associated with the interaction report is transmitted 350 to a client device 110, allowing subsequent retrieval of the interaction report from the centralized service management module 120 using the identifier. The interaction record is transmitted 350 according to one or more settings included in the user profile of the identified user, allowing one or more settings to specify the communication protocol used for transmission 350. For example, the interaction report, or data associated with the interaction report, is transmitted 350 via SMS messaging or email, or other communication protocols, to one or more client devices 110 associated with the user based on one or more user profile settings to increase the likelihood of user receipt of data associated with the interaction report. Thus, user profiles in the user data store 220 allow customization of communication protocol, or protocols, used to transmit 350 the interaction report or data associated with the interaction report, based on individual user preferences.

The individualized healthcare management module 130, or centralized service management module 120, then receives 360 a response to the interaction from a client device 110 via the interface module 210 including data or information associated with the interaction report. For example, the response confirms that the user is able to physically arrive in an office associated with the service provider 160 at a date and time specified by the appointment request, the response requests an appointment with a service provider 160, a response confirms receipt of the interaction by a client device 110 or exchanges data between a client device 110 and a service provider 160. In an embodiment, the response includes data, such as medical history, demographic information or other data associated with receipt of a service.

Upon receiving 360 the response the centralized service management module 120 stores 370 the response in the user data store 220. For example, the response is associated with a user profile included in the user data store 220 by retrieving a user identifier from the response and identifying the corresponding user profile from the user data store 220. The centralized service management module 120, or individualized healthcare management module 130, transmits 380 the response to the service provider 160 using the interface module 210 or the data bridge 280. In an embodiment, the centralized service management module 120, or individualized healthcare management module 130, also retrieves data describing a user's medical history, insurance information, demographic information or other data supplied by a user from a user profile included in the user data store 220 and transmits 380 the retrieved data to a service provider 160 Alternatively, the centralized service management module 120 retrieves data from a user profile provided by one or more service providers 160 which previously provided healthcare services to the user and transmits 380 the retrieved data to a service provider 160.

For example, as a plurality of independent service providers 160 provide services or products to a user, each of the independent service providers 160 transmit information about the provided services or products, such as a the results of a treatment, user comments regarding the treatment or product, suggested follow-up treatments or similar information, to the centralized service management module 120, which stores the information in a user profile. In one embodiment, the centralized service management module 120 verifies the authenticity of the received data, such as by examining a cryptographic signature associated with the received data. Hence, the centralized service management module 120 stores from various independent service providers 160 in a user profile, providing a central location for detailed records of a user's healthcare history while also verifying the integrity of the information through data authentication, allowing various independent service providers 160 to exchange information between themselves using the centralized service management module 120.

Settings in the user profile allow the user to specify a subset of the user data that is transmitted 380 by the centralized service management module 120 and a different subset of the user data that is not transmitted by the centralized service management module 120. For example, a setting indicates that data received from a pharmacy is transmitted 380 to a service provider 160 and a second setting indicates that data from an insurance provider 150 is not transmitted to the service provider 160. Hence, the user controls which data associated with the user profile is transmitted 380 to various independent service providers 160. Thus, the centralized service management module 120 transmits 380 data to different independent service providers 160 according to the user profile to expedite the user's receipt of products or services from different service providers 160 by simplifying exchange of user data between independent service providers 160 while maintaining the user's control over data privacy.

Figure 4:
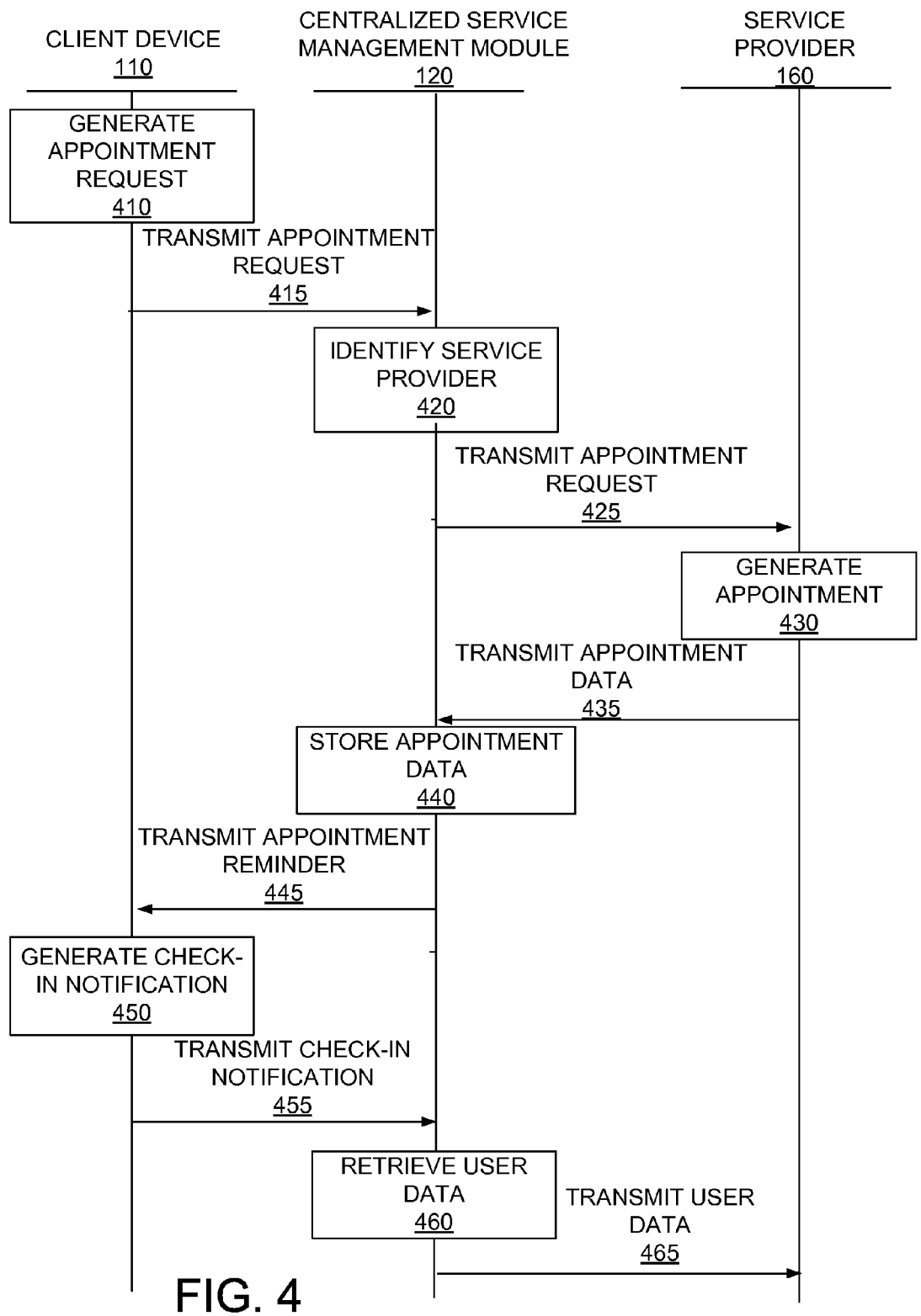
FIG. 4 is an event diagram of a method for scheduling a healthcare service appointment according to an embodiment of the present invention.
Figure 5:
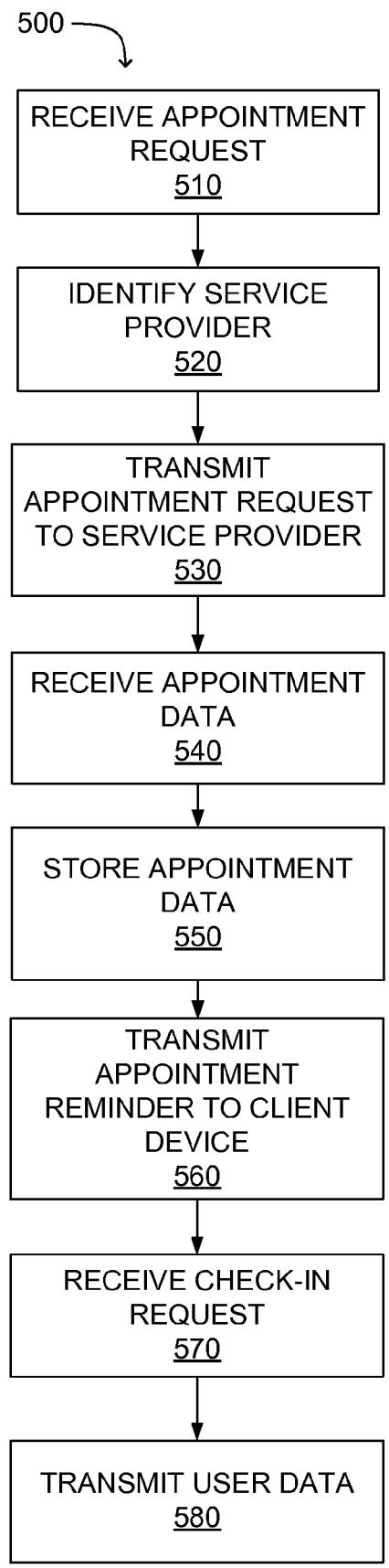
FIG. 5 is a flow chart of a method for healthcare service scheduling by an individualized healthcare management module according to an embodiment of the present invention.

FIGS. 4 and 5 below further describe example operation of the method 300 using scheduling of an appointment with a service provider 160 using an appointment request as a particular example of an interaction report. However, use of appointment scheduling is merely a single example of an interaction report and the method described above with respect to FIG. 3 allows multiple types of interaction reports describing various types of interactions between one or more client devices 110 and a plurality of independent service providers 160, such as recommendations of healthcare treatments, acquisition of prescription refills, reminders of scheduled treatments, notification of diagnostic or laboratory results or any other data associated with obtaining healthcare products or services the plurality of independent service providers 160.

FIG. 4 is an event diagram of a method for scheduling a healthcare service appointment according to an embodiment of the present invention. For purposes of illustration, FIG. 4 depicts interaction between a client device 110, a centralized service management module 120 and a service provider 160 other embodiments, multiple client devices 110 and multiple service providers 160, healthcare service providers 140 and/or insurance providers 150 communicate with each other in addition to communicating with the centralized service management module 120.

Initially, the client device 110 generates 410 an appointment request, which is a single example of an interaction report, from a user. In one embodiment, a user accesses a healthcare application operating on the client device 110 or accesses a healthcare website using the client device 110 and requests an appointment with a service provider 160, such as a physician's office, a laboratory, a clinic, a pharmacy or other healthcare service provider 140 or service provider 140 associated with healthcare treatment. For example, a user uses the client device 110 to schedule an appointment with a physician's office for a checkup or schedule an appointment with a laboratory for testing.

The appointment request includes data identifying the service provider 160, such as a provider identification number or other data describing the service provider 160, data identifying the user requesting the appointment, such as a healthcare consumer identifier, a login name, an email address, a phone number or other data uniquely identifying the healthcare consumer and data describing the service requested, such as a code associated with a healthcare procedure or a text description of the service or product requested. In an embodiment, the appointment request includes additional data, such as a desired date or time for the service, a range of dates or times for the service, a maximum distance between the service provider 160 and the client device 110 or user's residence or other data associated with scheduling an appointment with a service provider 160. In one embodiment, a user initiates the appointment request using the client device 110. Alternatively, the centralized service management module 120 transmits a notification message to the client device 110 using the network 170, and a user requests 310 an appointment responsive to receiving the notification message.

Hence, the centralized service management module 120 allows a user or a service provider 160 to schedule an appointment with the service provider 160 or an independent service provider 160. For example, a service provider 160 associated with a general practitioner, such as a family doctor, may access the centralized service management module 120 on a user's behalf and schedule the user an appointment with a service provider 160 associated with a specialist. Using the centralized service management module 120 allows the service provider 160 associated with the general practitioner to easily communicate data associated with the user to the service provider 160 associated with the specialist. As the centralized service management module 120 includes a user profile associated with the user, data from the user profile is communicated to the service provider associated with the specialist 160. Additionally, the service provider 160 associated with the general practitioner transmits data describing test results or diagnosis notes associated with the user to the centralized service management module 120, which stores and associates the data with the user profile, allowing the service provider 160 associated with the specialist to retrieve the data from the service provider 160 associated with the general practitioner by accessing the user profile stored by the centralized service management module 120. As another example, a nurse practitioner associated with a service provider 160 may call, email or otherwise contact a user to suggest that the user visit the service provider 160. Responsive to this contact, the user generates 410 an appointment request using a client device 110, which is subsequently used by the centralized service management module 120 and the service provider 160 to schedule an appointment for the user.

The appointment request is then transmitted 415 to the centralized service management module 120 using the network 170. The centralized service management module 120 uses the controller 285 in the individualized healthcare management module 130 to identify 420 one or more service providers 160 coupled to the centralized service management module 120. The controller 285 identifies one or more service providers 160 using the data included in the appointment request. For example, the controller 285 compares the service identifier included in the appointment request with service identifiers stored in the storage module 240 or user data store 220 of the centralized service management module 120. Alternatively, the controller 285 filters a locally stored listing of service providers 160 using information in the appointment request, such as a desired date or time for the service, a range of dates or times for the service, a maximum distance between the service provider 160 and the client device 110 or other data included in the appointment request to identify 420 a service provider 160. In another embodiment, the centralized service management module 120 retrieves a user profile from the user data store 220 associated with a user identifier included in the appointment request and identifies 420 a service provider 160 identified in the user profile.

The centralized service management module 120 then transmits 325 the appointment request to the identified service provider 160 via network 170. In an embodiment, the centralized service management module 120 uses the data bridge 280 to reformat or otherwise modify the appointment request to a format associated with the service provider 160 prior to transmission 425. After receiving the appointment request, the service provider 160 generates 430 an appointment from data in the appointment request. In an embodiment, the service provider 160 schedules an appointment with the service provider 160 based on data, such as a requested date and time or a specified date and time range, included in the appointment request. Data associated with the scheduled appointment, such as a date and time, is transmitted 435 from the service provider 160 to the centralized service management module 120 using the network 170.

The centralized service management module 120 locally stores 440 the data associated with the appointment in the user data store 220 in a user profile associated with the user requesting the appointment. Alternatively, the centralized service management module 120 stores a link or other pointer to the service provider 160 as part of the user profile of the user requesting the appointment, so that accessing the link or other pointer allows the centralized service management module 120 to retrieve data associated with the appointment.

After storing 440 the data associated with the appointment, the centralized service management module 120 transmits 445 an appointment reminder to one or more client devices 110 associated with the user requesting the appointment via the network 170. In an embodiment, the appointment reminder is transmitted 445 at a user-specified time, such as one day prior to the scheduled appointment, one week prior to the scheduled appointment or at a time specified by a setting in a user profile stored by the user data store 210. Alternatively, the appointment reminder is transmitted 445 to one or more client devices 110 at a predetermined time interval specified by the event management module 280, such as two hours before the scheduled appointment time. Additionally, the appointment reminder is transmitted 445 using one or more communication protocols according to settings included in a user profile. For example, the appointment reminder is transmitted 445 via SMS messaging or email, or transmitted using multiple communication channels according to user settings, increasing the likelihood that the user receives the appointment reminder at a client device 110.

In other embodiments, the centralized service management module 120 transmits information from a service provider 160 in addition to an appointment reminder. For example, the centralized service management module 120 receives a delay notification message from a service provider 160 indicating that the service provider 160 is unable to provide services or products to the user at the originally scheduled time, but is able to accommodate the user at a later time. This delay notification is transmitted from the centralized service management module 120 to a client device 110, allowing a user to delay arrival at an office associated with the service provider 160. Hence, the centralized service management module 120 allows a service provider 160 to provide users with current information to further reduce the time users wait for services.

Upon receiving the appointment reminder, the user generates 450 a check-in notification from a client device 110. The check-in notification confirms that the user is able to be physically present in an office associated with the service provider 160 at the date and time indicated by the appointment reminder. The check-in notification is then transmitted 455 from the client device 110 to the centralized service management module 120 using the network 170.

Upon receiving the check-in notification, the centralized service management module 120 retrieves 460 user data from the user data store 220. In an embodiment, the centralized service management module 120 stores service provider 160 preferences in the event management module 280, allowing individual service providers 160 to specify how far in advance users may check-in for an appointment. For example, a service provider 160 may allow users to check-in twenty-four hours in advance of a scheduled appointment while another service provider allows users to check-in only three hours prior to a scheduled appointment. By maintaining preferences for individual service providers 160, the centralized service management module 120 simplifies communication between a user and different service providers.

In an embodiment, the centralized service management module 120 retrieves 460 data from the user data store 220 describing a user's medical history, medication history, insurance information, demographic information or other data supplied by a user. Alternatively, the centralized service management module 120 retrieves 460 data from a user profile provided by one or more service providers 160 which previously provided healthcare services to the user. For example, as one or more service providers 160 provide services or products to a user, the one or more service providers 160 transmit information about the provided services or products, such as a the results of a treatment, user comments regarding the treatment or product, suggested follow-up treatments or similar information, to the centralized service management module 120, which stores the information in a user profile.

In one embodiment, information from a service provider 160 is cryptographically signed, or otherwise authenticated, by the service provider 160 to indicate the source of the data. Hence, the centralized service management module 120 may retrieve 460 data from a user profile received from various service providers 160 and verify the accuracy of the received data using the cryptographic signature or other authentication data associated with the received data. Hence, the centralized service management module 120 allows the service provider 160 to authenticate the source of the retrieved data.

When the centralized service management module 120 retrieves 460 user data, settings included in the user profile specify a subset of the user data for retrieval 460 and a subset of the user data that is not retrieved. For example, a user setting identifies user profile information from a pharmacy for retrieval 460 and identifies user profile information from an insurance provider 150 that is not retrieved. Hence, the settings allow user control of user profile data retrieved 460 for use by the service provider. The retrieved user data is then transmitted 465 to the service provider 160. Thus, the centralized service management module 120 transmits 465 data from a user profile to the service provider 160 to expedite the user's receipt of products or services from the service provider 160.

By transmitting user data from the centralized service management module 120 to the service provider 160 responsive to the check-in notification, the centralized service management module 120 allows the service provider 160 to have user data applicable to the scheduled appointment before the user arrives at the service provider 160 at the scheduled time. For example, the centralized service management module 120 transmits 465 insurance information, demographic information or prior medical test results to the service provider 160 to prevent the user from completing forms or providing information while at the service provider 160. Hence, the user may arrive at the service provider 160 at the scheduled time and receive a product or service without waiting, simplifying receipt of healthcare products or services by reducing wait times.

FIG. 5 is a flow chart of a method 500 for healthcare service scheduling by an individualized healthcare management module 130 according to an embodiment of the present invention. In an embodiment, the steps of the method 500 are implemented by a processor included in the centralized service management module 120 executing software or firmware instructions that cause the described actions. Those of skill in the art will recognize that one or more of the methods may be implemented in embodiments of hardware and/or software or combinations thereof. For example, instructions for performing the described actions are embodied or stored within a computer readable medium. Furthermore, those of skill in the art will recognize that other embodiments can perform the steps of FIG. 5 in different orders. Moreover, other embodiments can include different and/or additional steps than the ones described here.

The centralized service management module 120 receives 510 an appointment request from a client device 110 via the interface module 210. In one embodiment, the appointment request includes data identifying a service provider 160, such as a provider identification number or other data associated with the service provider 160, data identifying the user requesting the appointment, such as a healthcare consumer identifier, a login name, an email address, a phone number or other data uniquely identifying the healthcare consumer and data describing the service requested, such as a code associated with a medical procedure or a text description of the service requested. In an embodiment, the appointment request includes additional data, such as a desired date or time for the service, a range of dates or times for the service, a maximum distance between the service provider 160 and the client device 110 or other data associated with scheduling an appointment with a service provider 160.

The controller 285 included in the individualized healthcare management module 130 within the centralized service management module 120 then identifies 520 a service provider 160 associated with the received appointment request using the data included in the appointment request. For example, the controller 285 compares the service identifier included in the appointment request with service identifiers stored in the storage module 240 of the centralized service management module 120. Alternatively, the controller 285 filters a listing of service providers 160 included in the storage module 240 using information in the appointment request, such as a desired date or time for the service, a range of dates or times for the service, a maximum distance between the service provider 160 and the client device 110 or user address or other data associated with scheduling an appointment with a service provider 160, to identify 520 a service provider. In another embodiment, the centralized service management module 120 retrieves a user profile from the user data store 220 associated with a user identifier included in the appointment request and identifies 520 a service provider 160 associated with the user profile.

The centralized service management module 120 then transmits 530 the appointment request to the identified service provider 160 via the interface module 210 or the data bridge 260. In an embodiment, the centralized service management module 120 reformats or otherwise modifies the appointment request to simplify review by the service provider 160 prior to transmission 530. After the service provider 160 schedules an appointment using the appointment request, the centralized service management module 120 receives 540 data associated with the scheduled appointment, such as a date and time, and stores 550 the data associated with the appointment. In an embodiment, the centralized service management module 120 stores 550 the data associated with the appointment in the user data store 220 in a user profile associated with the user requesting the appointment. Alternatively, the centralized service management module 120 stores a link or other pointer to the service provider 160 in the user profile of the user requesting the appointment, so that accessing the link or other pointer retrieves data associated with the appointment.

After storing 550 the data associated with the appointment in the storage module 240 or user data store 220, the centralized service management module 120 transmits 560 an appointment reminder to one or more client devices 110 associated with the user requesting the appointment using the interface module 210. In an embodiment, the appointment reminder is transmitted 560 at a time specified by a setting in the user profile, such as one day prior to the scheduled appointment, one week prior to the scheduled appointment. The appointment reminder is transmitted 560 using one or more communication protocols specified by settings in the user profile. For example, the appointment reminder is transmitted 560 via SMS messaging or email, or transmitted using multiple communication channels according to user settings to increase the likelihood of user receipt of the appointment reminder. In one embodiment, an appointment reminder is transmitted 560 at multiple intervals until a check-in request is received 570, so that a user is reminded until acknowledging awareness of the appointment. Thus, user profiles in the user data store 210 allow customization of communication protocol, or protocols, used to transmit 560 the appointment reminder to increase the likelihood that the user is reminded of the scheduled appointment.

The centralized service management module 120 then receives 570 a check-in request from a client device 110 via the interface module 210 confirming that the user is able to physically arrive in an office associated with the service provider 160 at the date and time specified by the appointment request. Upon receiving 570 the check-in notification, the centralized service management module 120 transmits 580 data from the user data store 220 to the service provider 160 using the interface module 210 or the data bridge 280. In an embodiment, the centralized service management module 120 retrieves data describing a user's medical history, insurance information, demographic information or other data supplied by a user associated with healthcare services and transmits 580 the retrieved data to a service provider 160. Alternatively, the centralized service management module 120 retrieves data from a user profile provided by one or more service providers 160 which previously provided healthcare services to the user and transmits 580 the retrieved data to a service provider 160.

For example, as one or more service providers 160 provide services or products to a user, the one or more service providers 160 transmit information about the provided services or products, such as a the results of a treatment, user comments regarding the treatment or product, suggested follow-up treatments or similar information, to the centralized service management module 120, which stores the information in a user profile. In one embodiment, the centralized service management module 120 verifies the authenticity of the received data, such as by examining a cryptographic signature associated with the received data. Hence, the centralized service management module 120 may store data in a user profile that was received from various service providers 160 to provide a central location for detailed records of a user's healthcare history while also verifying the integrity of the information through data authentication.

Settings in the user profile allow the user to specify a subset of the user data that is transmitted 580 and a different subset of the user data that is not transmitted. For example, a setting indicates that data received from a pharmacy is transmitted 580 to a service provider 160 and a second setting indicates that data from an insurance provider 150 is not transmitted.

Hence, the user controls which data associated with the user profile is transmitted 580 to various service providers 160. Thus, the centralized service management module 120 transmits 580 data to the service provider 160 according to the user profile to expedite the user's receipt of products or services from the service provider 160 while maintaining the user's control over data privacy.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats. Furthermore, as will be apparent to one of ordinary skill in the relevant art, the modules, routines, features, attributes, methodologies and other aspects of the present invention can be implemented as software, hardware, firmware or any combination of the three. Of course, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

What is claimed is:

1. A system for managing a healthcare service or product comprising:
   one or more processors; and
   a centralized service management module stored on a memory and executable by the one or more processors, the centralized service management module communicatively coupled to a client device and a plurality of independent service providers that provide the healthcare product or service, the centralized service management module for:
      receiving an interaction record from the client device that includes an appointment request identifying a first time for receipt of the healthcare product or service, and a distance for receiving the healthcare product or service,
      storing a user profile including data describing healthcare information associated with a user of the client device, results of a treatment from a first service provider and suggested follow-up treatments,
      identifying the first service provider associated with the interaction record from the plurality of independent service providers based on at least one of the first time and determining that the first service provider is located within the distance from the client device,
      transmitting the interaction record to the first service provider,
      transmitting to the client device an appointment reminder including data describing a scheduled appointment associated with the appointment request and the first service provider's preference specifying a time window prior to a start of the scheduled appointment for sending a check-in request,
      transmitting a delay notification to the client device for rescheduling the scheduled appointment to a second time,
      responsive to receiving the check-in request from the client device after the appointment reminder,
         retrieving data from the user profile describing healthcare information associated with the appointment request, and
         transmitting the retrieved data from the user profile to the first service provider prior to the user's arrival at the first service provider, and
      responsive to failing to receive the check-in request,
         transmitting a miss notification to the client device for notifying the user that the scheduled appointment was missed and prompting the user to reschedule the scheduled appointment to a third time.

2. The system of claim 1, wherein the interaction record includes an identifier associated with the user, an identifier describing the first service provider, a date associated with the healthcare product or service, the first time associated with the healthcare product or service and a text description of the healthcare product or service.

3. The system of claim 1, wherein the interaction record comprises the appointment request identifying the first time for receipt of the healthcare service or product, the first service provider and the user.

4. The system of claim 1, wherein the centralized service management module includes a user data store for storing data received from the first service provider describing the healthcare product or service associated with the interaction record in the user profile associated with the user of the client device.

5. The system of claim 4, wherein the centralized service management module includes an individualized healthcare management module coupled to the user data store, the individualized healthcare management module for receiving data from the first service provider, identifying the user associated with the data from the first service provider and transmitting the data from the first service provider to the client device using a plurality of settings included in the user profile associated with the user of the client device.

6. The system of claim 5, wherein the plurality of settings included in the user profile associated with the user of the client device identify a subset of the data from the first service provider for transmission to the client device.

7. The system of claim 5, wherein the plurality of settings included in the user profile associated with the user of the client device identify a subset of the data from the first service provider for transmission to a second service provider.

8. The system of claim 5 wherein the plurality of settings included in the user profile identify a communication protocol for transmitting the data from the first service provider to the client device.

9. The system of claim 4, wherein the user data store stores data associated with the user of the client device received from a second service provider which is independent from the first service provider.

10. The system of claim 9, wherein the data received from the second service provider is authenticated by the second service provider.

11. The system of claim 1, wherein the plurality of independent service providers comprise at least one of a hospital, a pharmacy, a physician office, a clinic, a medical laboratory, a physician rating service, a hospital rating service, a personal health record store, a health coach, a health bank, a health information provider, a health savings account, a flexible savings account, a health reimbursement arrangement, a medical savings account, a diagnostic imaging facility, an outpatient surgery facility, a long-term care facility, an urgent care facility and an insurance provider.

12. A method for managing a healthcare product or service comprising:
receiving, with one or more processors, an interaction record associated with the healthcare product or service from a client device, the interaction record including an appointment request identifying a first time for receipt of the healthcare product or service and a distance for receiving the healthcare product or service;
identifying, with the one or more processors, a first service provider associated with the interaction record, the first service provider identified from a plurality of independent service providers based on at least one of the first time and determining that the first service provider is located within the distance from the client device;
identifying, with the one or more processors, a user profile associated with the interaction record, the user profile including data describing healthcare information associated with a user of the client device;
transmitting, with the one or more processors, the interaction record to the first service provider associated with the interaction record;
receiving, with the one or more processors, data from the first service provider associated with the interaction record, the data describing the healthcare product or service associated with the interaction record and user profile data including results of a treatment from the first service provider and suggested follow-up treatments;
storing, with the one or more processors, the received data from the first service provider describing the healthcare product or service associated with the interaction record in the identified user profile;
transmitting, with the one or more processors, an appointment reminder including data describing a scheduled appointment associated with the appointment request and the first service provider's preference specifying a time window prior to a start of the scheduled appointment for sending a check-in request to the client device;
transmitting, with the one or more processors, a delay notification to the client device for rescheduling the scheduled appointment to a second time;
responsive to receiving, with the one or more processors, a check-in request from the client device after the appointment reminder,
retrieving, with the one or more processors, data from the user profile describing healthcare information associated with the appointment request, and
transmitting, with the one or more processors, the retrieved data from the user profile to the first service provider prior to the user's arrival at the first service provider; and
responsive to failing to receive the check-in request, transmitting a miss notification to the client device for notifying the user that the scheduled appointment was missed and prompting the user to reschedule the scheduled appointment to a third time.

13. The method of claim 12, wherein the interaction record includes an identifier associated with the user, an identifier describing the first service provider, a date associated with the healthcare product or service, the first time associated with the healthcare product or service and a text description of the healthcare product or service.

14. The method of claim 12, wherein the interaction record comprises the appointment request identifying the first time for receipt of the healthcare product or service, the healthcare product or service, the first service provider and the user.

15. The method of claim 14, further comprising:
transmitting the appointment reminder to the client device at multiple intervals until the check-in request is received.

16. The method of claim 12, wherein retrieving the data from the user profile describing healthcare information associated with the appointment request comprises:
identifying a subset of the data from the user profile according to a plurality of settings included in the user profile; and
retrieving the subset of the data from the user profile.

17. The method of claim 12, wherein transmitting the appointment reminder including data describing the scheduled appointment to the client device comprises:
transmitting a short message service (SMS) message to the client device.

18. The method of claim 12, wherein transmitting the appointment reminder including data describing the scheduled appointment to the client device comprises:
transmitting an email message to the client device.

19. The method of claim 12, wherein transmitting the appointment reminder including data describing the scheduled appointment to the client device comprises:
initiating a telephone call to the client device.

20. The method of claim 12, wherein the user profile identifies a communication protocol for transmitting data associated with the interaction record received from the first service provider to the client device.

21. The method of claim 12, further comprising:
receiving data from a second service provider associated with the healthcare product or service, the second service provider being independent from the first service provider;
associating the data from the second service provider with the user profile; and
storing the data from the second service provider in the user profile.

22. The method of claim 21, wherein the data from the second service provider comprises data authenticated by the second service provider.

23. The method of claim 21, further comprising:
associating a setting in the user profile with the data from the second service provider, the setting determining whether the data from the second service provider is accessible by one or more additional service providers, the one or more additional service providers being independent from the first service provider and the second service provider.

24. The method of claim 12, wherein the plurality of independent service providers comprise at least one of a hospital, a pharmacy, a physician office, a clinic, a medical laboratory, a physician rating service, a hospital rating service, a personal health record store, a health coach, a health bank, a health information provider, a health savings account, a flexible savings account, a health reimbursement arrangement, a medical savings account, a diagnostic imaging facility, an outpatient surgery facility, a long-term care facility, an urgent care facility and an insurance provider.

25. A computer program product comprising a computer readable storage medium storing computer executable code for managing a healthcare product or service, the computer executable code performing the steps of:
- receiving an interaction record associated with the healthcare product or service from a client device, the interaction record including an appointment request identifying a first time for receipt of the healthcare product or service and a distance for receiving the healthcare product or service;
- identifying a first service provider associated with the interaction record, the first service provider identified from a plurality of independent service providers based on at least one of the first time and determining that the first service provider is located within the distance from the client device;
- identifying a user profile associated with the interaction record, the user profile including data describing healthcare information associated with a user of the client device;
- transmitting the interaction record to the first service provider associated with the interaction record;
- receiving data from the first service provider associated with the interaction record, the data describing the healthcare product or service associated with the interaction record and user profile information including results of a treatment from the first service provider and suggested follow-up treatments;
- storing the received data from the first service provider describing the healthcare product or service associated with the interaction record in the identified user profile;
- transmitting an appointment reminder including data describing a scheduled appointment associated with the appointment request and the first service provider's preference specifying a time window prior to a start of the scheduled appointment for sending a check-in request to the client device;
- transmitting a delay notification to the client device for rescheduling the scheduled appointment to a second time;
- responsive to receiving a check-in request from the client device after the appointment reminder,
  - retrieving data from the user profile describing healthcare information associated with the appointment request; and
  - transmitting the retrieved data from the user profile to the first service provider prior to the user's arrival at the first service provider; and
- responsive to failing to receive the check-in request,
  - transmitting a miss notification to the client device for notifying the user that the scheduled appointment was missed and prompting the user to reschedule the scheduled appointment to a third time.

26. The computer program product of claim 25, wherein the interaction record includes an identifier associated with the user, an identifier describing the first service provider, a date associated with the healthcare product or service, the first time associated with the healthcare product or service, and a text description of the healthcare product or service.

27. The computer program product of claim 25, wherein the interaction record comprises the appointment request identifying the first time for receipt of the healthcare product or service, the healthcare product or service, the first service provider and the user.

28. The computer program product of claim 27, wherein the computer executable code further performs the steps of:
- transmitting the appointment reminder to the client device at multiple intervals until the check-in request is received.

29. The computer program product of claim 25, wherein retrieving the data from the user profile describing healthcare information associated with the appointment request comprises:
- identifying a subset of the data from the user profile according to a plurality of settings included in the user profile; and
- retrieving the subset of the data from the user profile.

30. The computer program product of claim 25, wherein transmitting the appointment reminder including data describing the scheduled appointment to the client device comprises:
- transmitting a short message service (SMS) message to the client device.

31. The computer program product of claim 25, wherein transmitting the appointment reminder including data describing the scheduled appointment to the client device comprises:
- transmitting an email message to the client device.

32. The computer program product of claim 25, wherein transmitting the appointment reminder including data describing the scheduled appointment to the client device comprises:
- initiating a telephone call to the client device.

33. The computer program product of claim 25, wherein the user profile identifies a communication protocol for transmitting data associated with the interaction record received from the first service provider to the client device.

34. The computer program product of claim 25, wherein the computer executable code further performs the steps of:
- receiving data from a second service provider associated with the healthcare product or service, the second service provider being independent from the first service provider;
- associating the data from the second service provider with the user profile; and
- storing the data from the second service provider.

35. The computer program product of claim 34, wherein the data from the second service provider comprises data authenticated by the second service provider.

36. The computer program product of claim 34, wherein the computer executable code further performs the steps of:
- associating a setting in the user profile with the data from the second service provider, the setting determining whether the data from the second service provider is accessible by one or more additional service providers, the one or more additional service providers being independent from the first service provider and the second service provider.

37. The computer program product of claim 25, wherein the plurality of independent service providers comprise at least one of a hospital, a pharmacy, a physician office, a clinic, a medical laboratory, a physician rating service, a hospital rating service, a personal health record store, a health coach, a health bank, a health information provider, a health savings account, a flexible savings account, a health reimbursement arrangement, a medical savings account, a diagnostic imaging facility, an outpatient surgery facility, a long-term care facility, an urgent care facility and an insurance provider.

38. A method for managing a healthcare product or service comprising:

receiving, with one or more processors, an interaction record associated with the healthcare product or service from a service provider that includes an appointment request identifying a first time for receipt of the healthcare product or service and a distance for receiving the healthcare product or service;

identifying, with the one or more processors, a user profile associated with the interaction record, the user profile including data describing healthcare information associated with a user of a client device;

storing, with the one or more processors, the interaction record in the user profile;

transmitting, with the one or more processors, the interaction record to the client device associated with the user profile based on a setting included in the user profile, the setting included in the user profile identifying a plurality of communication protocols;

transmitting, with the one or more processors, an appointment reminder including data describing a scheduled appointment associated with the appointment request and the first service provider's preference specifying a time window prior to a start of the scheduled appointment for sending a check-in request to the client device;

transmitting, with the one or more processors, a delay notification to the client device for rescheduling the scheduled appointment to a second time;

receiving, with the one or more processors, a check-in request from the client device responsive to the appointment reminder and the user being able to take the scheduled appointment, the received check-in request being associated with the interaction record;

responsive to receiving the check-in request, retrieving, with the one or more processors, healthcare information associated with the appointment request;

transmitting, with the one or more processors, the retrieved healthcare information from the user profile to the service provider prior to the user's arrival at the service provider; and receiving, with the one or more processors, user profile information from the service provider that includes results of a treatment and suggested follow-up treatments; and responsive to failing to receive the check-in request, transmitting a miss notification to the client device for notifying the user that the scheduled appointment was missed and prompting the user to reschedule the scheduled appointment to a third time.

* * * * *